US012807553B2

(12) United States Patent
Breidenstein

(10) Patent No.: US 12,807,553 B2
(45) Date of Patent: Nov. 24, 2026

(54) COMBINED DIRECT METHANE TO METHANOL AND SYNGAS TO HYDROGEN

(71) Applicant: GAS TECHNOLOGIES LLC, Walloon Lake, MI (US)

(72) Inventor: Walter Breidenstein, Boyne Falls, MI (US)

(73) Assignee: GasTechno Corp., Boyne Falls, MI (US)

( * ) Notice: Subject to any disclaimer, the term of this patent is extended or adjusted under 35 U.S.C. 154(b) by 837 days.

(21) Appl. No.: 18/015,227

(22) PCT Filed: Jul. 9, 2021

(86) PCT No.: PCT/US2021/041121
§ 371 (c)(1),
(2) Date: Jan. 9, 2023

(87) PCT Pub. No.: WO2022/011283
PCT Pub. Date: Jan. 13, 2022

(65) Prior Publication Data
US 2023/0257330 A1 Aug. 17, 2023

Related U.S. Application Data

(60) Provisional application No. 63/049,883, filed on Jul. 9, 2020.

(51) Int. Cl.
*C07C 29/50* (2006.01)
*C01B 3/386* (2026.01)
*C07C 41/01* (2006.01)

(52) U.S. Cl.
CPC .............. *C07C 29/50* (2013.01); *C01B 3/386* (2013.01); *C07C 41/01* (2013.01)

(58) Field of Classification Search
CPC ......... C07C 29/50; C07C 41/01; C07C 31/04; C07C 31/08; C10G 2400/26; C10G 5/00; C10G 2/32; C01B 3/386; C10K 1/004; C10K 1/10; C10K 1/002
See application file for complete search history.

(56) References Cited

U.S. PATENT DOCUMENTS 9,255,051 B2 2/2016 Gaffney et al.
2009/0235587 A1 9/2009 Hawkes et al.
2015/0299074 A1 10/2015 Visser et al.
2017/0081602 A1 3/2017 Gaffney et al.

FOREIGN PATENT DOCUMENTS

WO 2014/145398 A1 9/2014
WO 2018081216 A1 5/2018
WO 2020/058859 A1 3/2020

OTHER PUBLICATIONS

Int'l Search Report and Written Opinion dated Dec. 29, 2021 for PCT Appn. No. PCT/US21/41121, 22 pgs.
Lim, Y. et al., "Optimal Design and Decision for Combined Steam Reforming Process with Dry Methane Reforming to Reuse CO2 as a Raw Material," Industrial & Engineering Chemisty Research, 51 (13), pp. 4982-4989.
1st Exam Report dtd May 26, 26 for IN Appn. No. 202317005935, 9 pgs.

*Primary Examiner* — Jafar F Parsa
(74) *Attorney, Agent, or Firm* — Brooks Kushman P.C.

(57) ABSTRACT

A system that combines partial hydrocarbon oxidation with methane reforming is provided. The system advantageously uses products or partial products from the partial hydrocarbon oxidation to form the syngas, mixture of alcohols and other oxygenated hydrocarbons.

25 Claims, 8 Drawing Sheets

| Mole Fraction | | | | |
|---|---|---|---|---|
| Gas type | Feed Gas | MiniGTL reactor Inlet stream (NG) | POX reactor inlet stream | POX reactor outlet stream |
| Methane | 0.59 | 0.73 | 0.51 | 0.16 |
| Ethane | 0.26 | 0.17 | 0.12 | 0.00 |
| Propane | 0.10 | 0.04 | 0.03 | 0.00 |
| i-Butane | 0.00 | 0.00 | 0.00 | 0.00 |
| n-Butane | 0.00 | 0.00 | 0.00 | 0.00 |
| i-Pentane | 0.00 | 0.00 | 0.00 | 0.00 |
| n-Pentane | 0.00 | 0.00 | 0.00 | 0.00 |
| 22-Mbutane | 0.00 | 0.00 | 0.00 | 0.00 |
| 23-Mbutane | 0.00 | 0.00 | 0.00 | 0.00 |
| 2-Mpentane | 0.00 | 0.00 | 0.00 | 0.00 |
| 2-E-1-C4ol | 0.00 | 0.00 | 0.00 | 0.00 |
| n-Hexane | 0.00 | 0.00 | 0.00 | 0.00 |
| n-Heptane | 0.00 | 0.00 | 0.00 | 0.00 |
| n-Octane | 0.00 | 0.00 | 0.00 | 0.00 |
| Ethanol | 0.00 | 0.00 | 0.00 | 0.00 |
| Methanol | 0.00 | 0.00 | 0.00 | 0.00 |
| CO2 | 0.02 | 0.01 | 0.01 | 0.01 |
| Oxygen | 0.00 | 0.00 | 0.30 | 0.00 |
| Nitrogen | 0.02 | 0.02 | 0.01 | 0.01 |
| Formaldehyde | 0.00 | 0.00 | 0.00 | 0.00 |
| CO | 0.00 | 0.01 | 0.01 | 0.31 |
| H2O | 0.00 | 0.00 | 0.00 | 0.02 |
| Hydrogen | 0.00 | 0.01 | 0.01 | 0.50 |
| Hemiformal_12* | 0.00 | 0.00 | 0.00 | 0.00 |
| Methylene glycol_12* | 0.00 | 0.00 | 0.00 | 0.00 |
| Hemiformal* | 0.00 | 0.00 | 0.00 | 0.00 |
| Methylene glycol* | 0.00 | 0.00 | 0.00 | 0.00 |

*Fig. 1B*

| | |
|---|---|
| Feed gas inlet stream(mmscfd) | 8 |
| MINI GTL inlet stream(mmscfd) | 7.54 |
| POX Reactor Inlet stream(mmscfd) | 6.85 |
| POX Reactor Outlet stream(mmscfd) | 12 |
| Oxygen inlet line MiniGTL(mmscfd) | 2.10 |
| Oxygen inlet line POX(mmscfd) | 2 |

*Fig. 1C*

| Natural gas feed stock | | |
|---|---|---|
| Parameters | With an additional POX reactor | Without POX reactor |
| | Inlet | Inlet |
| Temperature(°C) | 26.50 | 26.50 |
| Pressure (PSIA) | 300.00 | 300.00 |
| Molar flow NG (lbmol/hr) | 892.00 | 892.00 |
| Standard Nat Gas flow (mmscfd) | 8.00 | 8.00 |
| Standard Oxygen flow (mmscfd) | 4.10 | 2.10 |

*Fig. 1D*

| MiniGTL reactor | Inlet | Outlet |
|---|---|---|
| Temperature(°C) | 400 | 555 |
| Pressure (PSIA) | 1006 | 985 |
| NG Molar flow (lbmol/hr) | 829.8 | 8 |
| NG Standard Gas flow (mmscfd) | 7.54 | |
| Oxygen Standard Gas flow (mmscfd) | 2.10 | |

*Fig. 1E*

| POX reactor parameters | Inlet | Outlet |
|---|---|---|
| Temperature(°C) | 382 | 938.0 |
| Pressure (PSIA) | 256 | 226.0 |
| Molar flow (lbmol/hr) (NG+O2) | 754 | 1364.0 |
| Standard Gas flow (mmscfd) (NG+O2) | 6.85 | 12.4 |

*Fig. 1F*

| Mole Fraction | | | |
|---|---|---|---|
| Gas type | MiniGTL reactor Inlet stream (NG) | DRM reactor inlet stream | DRM reactor outlet stream |
| Methane | 0.732 | 0.43 | 0.055 |
| Ethane | 0.144 | 0.08 | 0.051 |
| Propane | 0.033 | 0.02 | 0.011 |
| i-Butane | 0.000 | 0.00 | 0.000 |
| n-Butane | 0.000 | 0.00 | 0.000 |
| i-Pentane | 0.000 | 0.00 | 0.000 |
| n-Pentane | 0.000 | 0.00 | 0.000 |
| 22-Mbutane | 0.000 | 0.00 | 0.000 |
| 23-Mbutane | 0.000 | 0.00 | 0.000 |
| 2-Mpentane | 0.000 | 0.00 | 0.000 |
| 2-E-1-C4ol | 0.000 | 0.00 | 0.000 |
| n-Hexane | 0.000 | 0.00 | 0.000 |
| n-Heptane | 0.000 | 0.00 | 0.000 |
| n-Octane | 0.000 | 0.00 | 0.000 |
| Ethanol | 0.002 | 0.00 | 0.001 |
| Methanol | 0.004 | 0.00 | 0.002 |
| CO2 | 0.002 | 0.40 | 0.035 |
| Oxygen | 0.000 | 0.00 | 0.000 |
| Nitrogen | 0.020 | 0.01 | 0.008 |
| Formaldehyde | 0.000 | 0.00 | 0.000 |
| CO | 0.029 | 0.02 | 0.234 |
| H2O | 0.000 | 0.00 | 0.367 |
| Hydrogen | 0.034 | 0.03 | 0.236 |
| Hemiformal_12* | 0.000 | 0.00 | 0.000 |
| Methylene glycol_12* | 0.000 | 0.00 | 0.000 |
| Hemiformal* | 0.000 | 0.00 | 0.000 |
| Methylene glycol* | 0.000 | 0.00 | 0.000 |

*Fig. 2B*

| Natural gas (NG) feed gas process conditions | |
|---|---|
| Temperature(F) | 80 |
| Pressure (PSIA) | 300 |
| Molar flow NG (lbmol/hr) | 212 |
| Standard Nat Gas flow (mmscfd) | 1.928 |
| Standard Oxygen flow (mmscfd) | 0.5535 |
| Molar flow Oxygen (lbmol/hr) | 60.89 |

*Fig. 2C*

| DRM reactor parameters | Inlet | Outlet |
|---|---|---|
| Temperature(F) | 977.6 | 977 |
| Pressure (PSIA) | 25 | 25 |
| Molar flow (lbmol/hr) | 22.8 | 35.98 |
| Standard Gas flow (mmscfd) | 0.2072 | 0.327 |

*Fig. 2D*

COMBINED DIRECT METHANE TO METHANOL AND SYNGAS TO HYDROGEN

CROSS-REFERENCE TO RELATED APPLICATIONS

This application is the U.S. national phase of PCT Appln. No. PCT/US2021/041121 filed Jul. 9, 2021, which claims the benefit of U.S. provisional application Ser. No. 63/049,883 filed Jul. 9, 2020, the disclosures of which are hereby incorporated in their entirety by reference herein.

TECHNICAL FIELD

In at least one aspect, the present invention is related to direct methane to methanol and syngas to hydrogen.

BACKGROUND

Autothermal and steam reforming of natural gas are currently two of the most expensive methods of producing hydrogen and carbon oxides. The gaseous mixture of hydrogen and carbon oxides (carbon monoxide) is hereinafter referred to as "synthetic gas" or "syngas." Syngas is useful as an intermediate for the manufacture of products such as hydrogen, ammonia, methanol or synthetic fuels. Currently, commercial methanol production is almost entirely based on reforming light hydrocarbons, especially methane, first to syngas, followed by syngas clean up, methanol synthesis, and methanol separation. This process has been the dominant route of methanol production since the 1920's. The entire process, however, is cumbersome with a high degree of complexity and associated costs. Therefore, a direct method has been developed using direct homogenous partial oxidation of methane to methanol (the "DHPO" method).

The DHPO method is, however generally limited by the need to balance high conversions and high selectivity to obtain the highest economic yields of methanol. In both catalytic and non-catalytic DHPO methods, the conversion process tends to create the co-products of aldehydes, alcohols, hydrogen, carbon oxides, and water.

Accordingly, there is a need for methods and apparatuses that can economically produce low cost methanol, synthesis gas and hydrogen.

SUMMARY

In at least one aspect, a method for preparing oxygenated hydrocarbons is provided. The method includes a step of combining a hydrocarbon feed gas stream and a recycle gas stream to form a first hydrocarbon-containing gas stream. The hydrocarbon feed gas stream is characterized by a first temperature $T_1$, the recycle gas stream is characterized by a second temperature $T_2$, and the first hydrocarbon-containing gas stream is characterized by a third temperature $T_3$. The first hydrocarbon-containing gas stream is preheated to form a second hydrocarbon-containing gas stream having a fourth temperature $T_4$ that is greater than the third temperature $T_3$. The second hydrocarbon-containing gas stream is reacted with an oxygen-containing gas stream in a partial oxidation reactor to form a first product stream. One or more liquid oxygenated hydrocarbons are separated and condensed from the first product stream. A fuel gas stream and the recycle gas stream are separated from the first product stream. A portion of the first hydrocarbon-containing gas stream and the second hydrocarbon-containing gas stream are combined to form a third hydrocarbon-containing gas stream having a fifth temperature that is between the third temperature and the fourth temperature. The third hydrocarbon-containing gas stream and oxygen are directed to a syngas reactor that converts the third hydrocarbon-containing gas stream to syngas and/or turquoise hydrogen. Finally, syngas and/or turquoise hydrogen is collected from the syngas reactor.

In another aspect, a method for preparing oxygenated hydrocarbons is provided. The method includes a step of combining a hydrocarbon feed gas stream and a $CO_2$ lean recycle gas stream to form a first hydrocarbon-containing gas stream. The hydrocarbon feed gas stream is characterized by a first temperature $T_1$, the $CO_2$ lean recycle gas stream is characterized by a second temperature $T_2$, and the first hydrocarbon-containing gas stream is characterized by a third temperature $T_2$. The first hydrocarbon-containing gas stream is preheated to form a second hydrocarbon-containing gas stream having a fourth temperature $T_4$ that is greater than the third temperature $T_3$. The second hydrocarbon-containing gas stream is reacted with a first oxygen-containing gas stream in a GTL reactor to form a first product stream. One or more liquid oxygenated hydrocarbons are separated and condensed from the first product stream. A fuel gas stream and a $CO_2$ rich recycle gas stream are separated from the first product stream. $CO_2$ is removed from the $CO_2$ rich recycle gas stream to form the $CO_2$ lean recycle gas stream. A portion of the $CO_2$ lean recycle gas stream is combined with a portion of the fuel gas stream to form a third hydrocarbon-containing gas stream. The third hydrocarbon-containing gas stream and a second oxygen-containing stream is directed to a syngas reactor (e.g., a DRM reactor) to form syngas and/or turquoise hydrogen. Finally, syngas is collected from the syngas reactor and/or turquoise hydrogen.

In another aspect, a combined POX and methanol forming system is provided. Advantages of a combined POX and MeOH system include: a major saving on CAPEX as combined process eliminates the need for a separate ASU; syngas production becomes significantly cheaper compared to a convention reforming process; GTL oxygen production is easily scalable to the POM feed requirements; downstream compatible syngas for FT; Diesel/gasoline or MeOH; Heat integration of the POX reactor also offers additional savings on the distillation of GTL products, and easily integrated to the MiniGTL plant with minimal utility requirement.

In another aspect, a system for producing syngas and/or turquoise hydrogen applying the methods herein is provided. The system includes a hydrocarbon feed gas stream source that provides hydrocarbon feed gas stream where the hydrocarbon feed gas stream has a first temperature and a recycle conduit through which a recycle gas stream flows where the recycle gas stream having a second temperature. A heating component preheats a first hydrocarbon-containing gas stream having a third temperature to form a second hydrocarbon-containing gas stream having a fourth temperature that is greater than the third temperature. The first hydrocarbon-containing gas stream includes a component selected from the group consisting of the hydrocarbon feed gas stream, the recycle gas stream, and combinations thereof. The system also includes a partial oxidation reactor for reacting the second hydrocarbon-containing gas stream with a first oxygen-containing gas stream to form a first product stream. The system also includes a 2-phase separator that separates and condenses one or more liquid oxygenated hydrocarbons from the first product stream. Advantageously, the 2-phase separator also separates a fuel gas stream and the recycle gas stream from the first product stream. A syngas reactor (e.g., a DRM reactor) receives a third hydrocarbon-containing gas stream and a second oxygen-containing gas stream. Characteristically, the syngas reactor converts the third hydrocarbon-containing gas stream to syngas and/or turquoise hydrogen, the third hydrocarbon-containing gas stream including a component selected from the group consisting of a portion of the first hydrocarbon-containing gas stream, a portion of the second hydrocarbon-containing gas stream, and combinations thereof where the third hydrocarbon-containing gas stream having a fifth temperature that is between the third temperature and the fourth temperature.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements and wherein:

FIG. 1B. An example of gas concentrations at the GLT reactor, the POX reactor inlet, and the POX reactor outlet for the system of FIG. 1A.

FIG. 1C. An example of flows for the system of FIG. 1A.

FIG. 1D. An example of natural gas feedstock parameters for the system of FIG. 1A.

FIG. 1E. An example of GLT reactor conditions for the system of FIG. 1A.

FIG. 1F. An example of POX reactor conditions for the system of FIG. 1A.

FIG. 2B. An example of gas concentrations at the GLT reactor, the DRM reactor inlet, and the DRM reactor outlet for the system of FIG. 2A.

FIG. 2C. An example of natural gas feed gas process conditions for the system of FIG. 2A.

FIG. 2D. An example of DRM reactor conditions for the system of FIG. 2A.

DETAILED DESCRIPTION

Figure 1A:
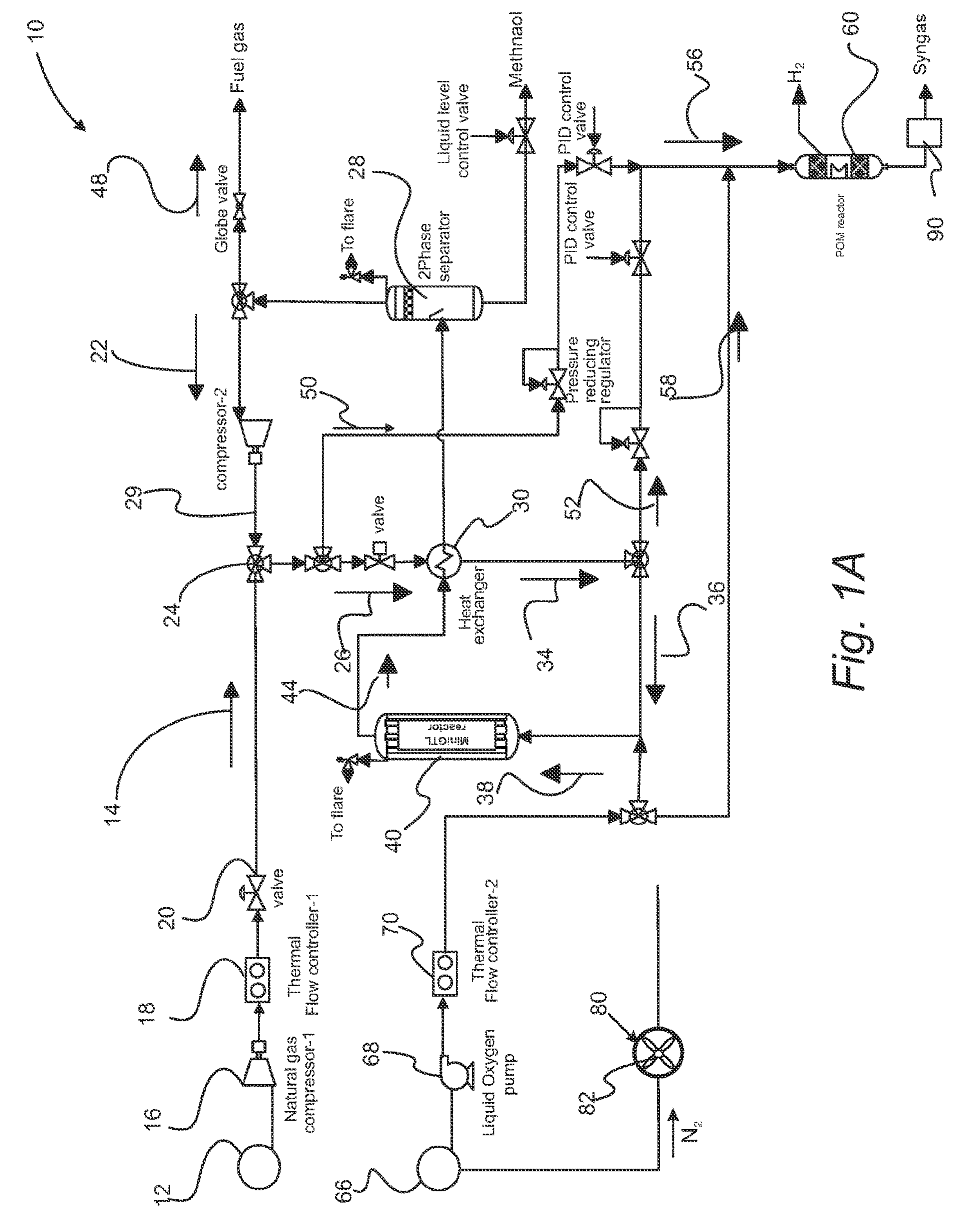
FIG. 1A. Schematic of a reactor for forming hydrocarbon oxygenates and syngas with a POX reactor.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e. the range from 95 to 105. Generally, when the term "about" is used, it can be expected that similar results or effects according to the invention can be obtained within a range of +/−5% of the indicated value.

As used herein, the term "and/or" means that either all or only one of the elements of said group may be present. For example, "A and/or B" shall mean "only A, or only B, or both A and B". In the case of "only A", the term also covers the possibility that B is absent. i.e. "only A, but not B".

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The phrase "composed of" means "including" or "consisting of." Typically, this phrase is used to denote that an object is formed from a material.

With respect to the terms "comprising," "consisting of," and "consisting essentially of," where one of these three terms is used herein, the presently disclosed and claimed subject matter can include the use of either of the other two terms.

The term "one or more" means "at least one" and the term "at least one" means "one or more." The terms "one or more" and "at least one" include "plurality" as a subset.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

In the examples set forth herein, concentrations, temperature, flow rates, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, flow rates and reaction conditions (e.g., pressure, pH, flow rates, etc.) can be practiced with plus or minus 30 percent of the values indicated rounded to or truncated to two significant figures of the value provided in the examples. In another refinement, concentrations, temperature, flow rates, and reaction conditions (e.g., pressure, pH, flow rates, etc.) can be practiced with plus or minus 10 percent of the values indicated rounded to or truncated to two significant figures of the value provided in the examples.

Figure 2A:
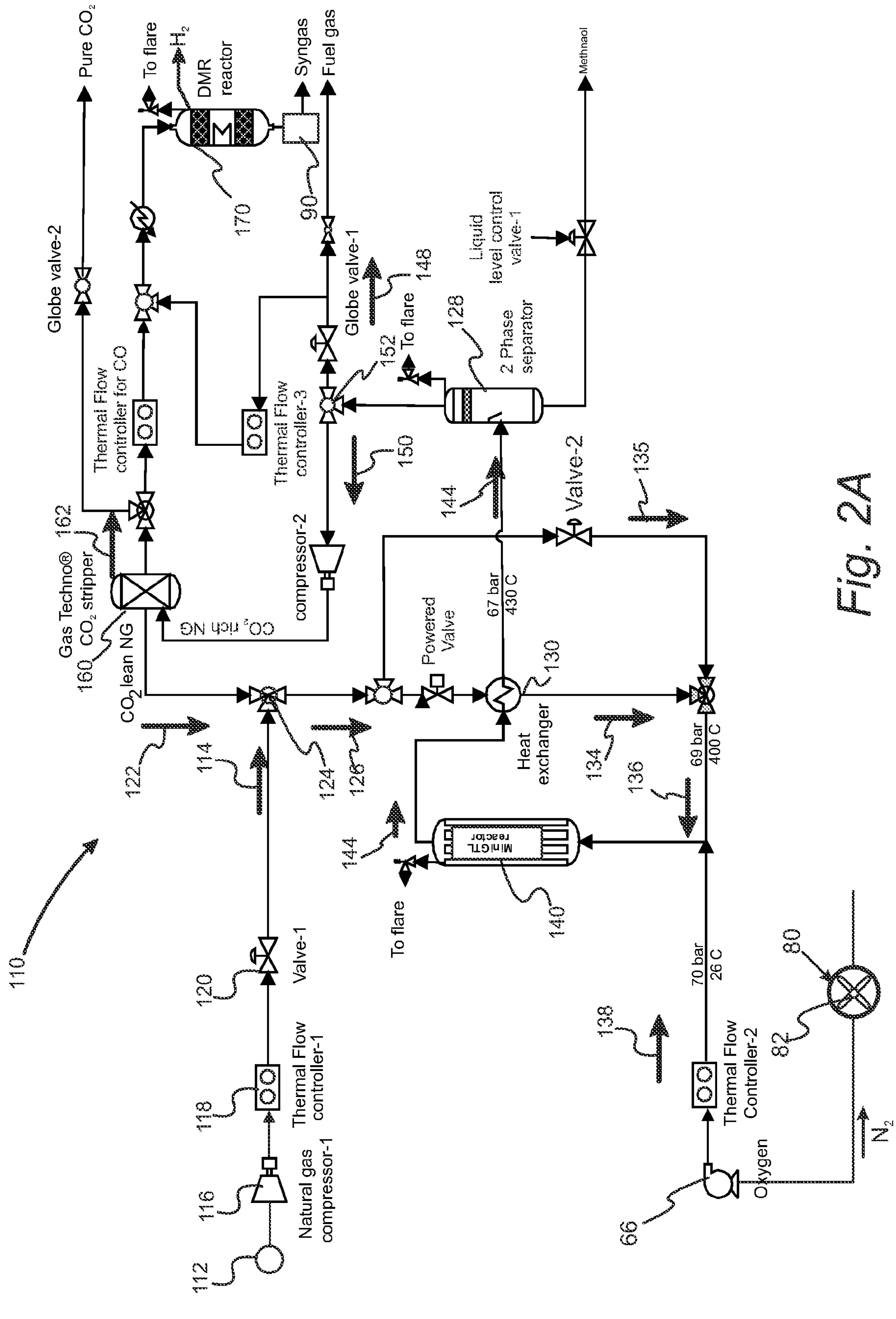
FIG. 2A. Schematic of a reactor for forming hydrocarbon oxygenates and syngas with a DMR reactor.
Figure 3:
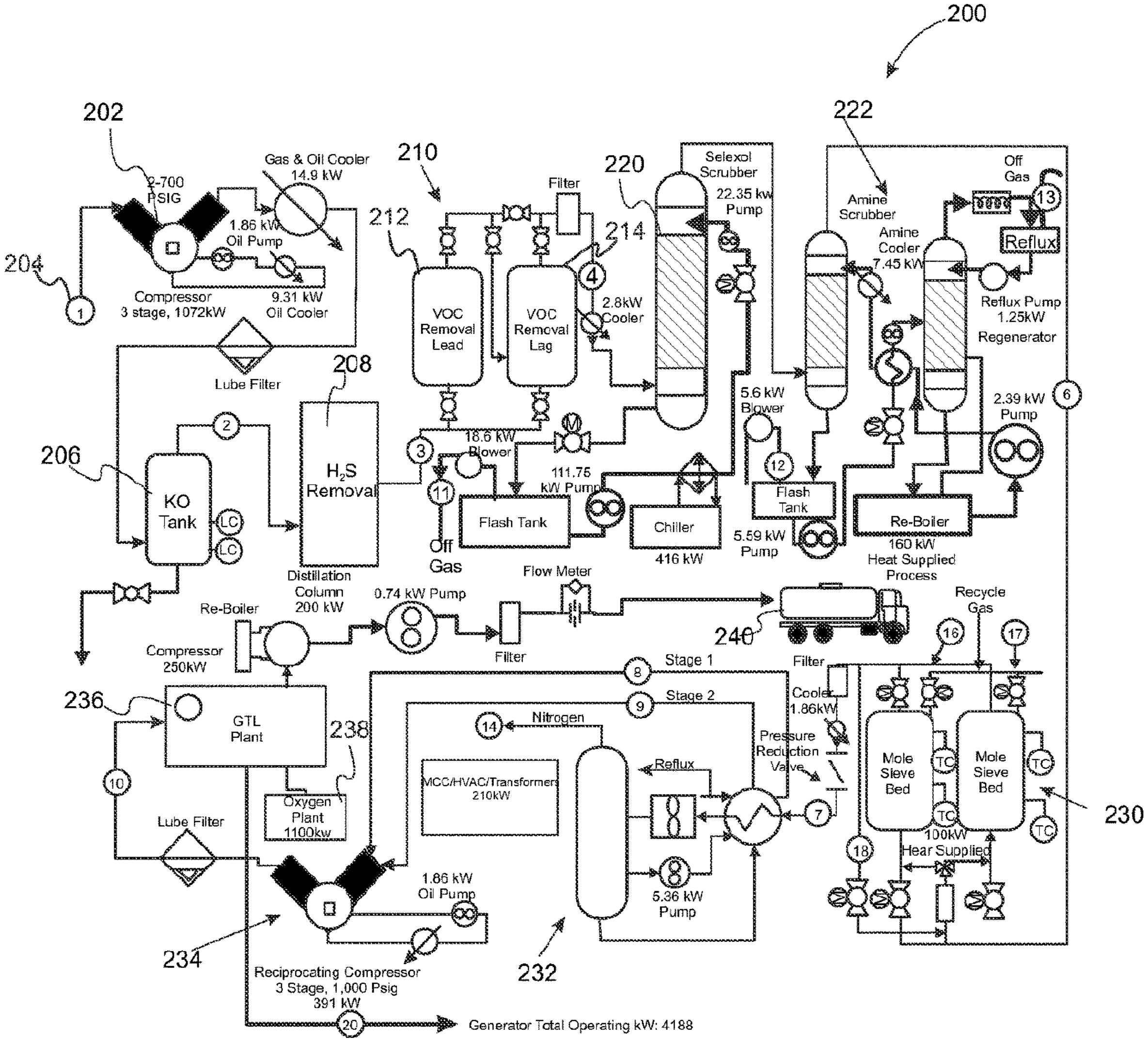
FIG. 3. Schematic of a system for biomass to renewable natural gas to methanol, DME, and hydrogen.

With respect to FIGS. 1A, 2A, and 3, lines with or without arrowhead drawn between components represent conduits through with fluids (e.g., liquids and/or gases can flow). Therefore, components connected with such lines are in fluid communication.

Abbreviations

"ag" means agricultural.

"ASU" means air separation unit.

"DME" means dimethyl ether.

"DMR" means dry methane reforming.

"GLT" means gas-to-liquids.

"MMSCFD" means million standard cubic feet per day.

"POM" means partial methane reforming.

"POX" means partial oxidation.

"PSA" means pressure swing absorption.

"VOC" means volatile organic compounds.

"WWTP" means waste water treatment plant.

Referring to FIGS. 1A and 2A, schematics of systems for preparing partial hydrocarbon oxygenates and/or syngas and/or turquoise hydrogen are provided. The figures shows the process components that are in fluid communication. Characteristically each of the systems depicted in FIGS. 1A and 2A combine to formation of methanol and optionally other oxygenates with the production of syngas and/or turquoise hydrogen.

With reference to FIG. 1A, a schematic of a system having a POM reactor is provided. System 10 includes source 12 of a hydrocarbon feedstock. Hydrocarbon feed gas stream 14 is established by natural gas compressor 16, thermal flow controller 18, and valve 20. Hydrocarbon feed gas stream 14 is characterized by a first temperature $T_1$ and a first pressure $P_1$. In a refinement, first temperature $T_1$ is from about 70 to 90° C. and the first pressure $P_1$ is from about 50 to 100 bar. Hydrocarbon feed gas stream 14 is combined with recycle gas stream 22 at three way valve or splitter 24 to form a first hydrocarbon-containing gas stream 26. Hydrocarbon feed gas stream 14 flows through conduit 15 while recycle gas stream 22 flow through recycle conduit 29 to three way valve or splitter 24 (or other gas combining component). Recycle gas stream 22 is characterized by a second temperature $T_2$ and a second pressure $P_2$. In a refinement, the second temperature $T_2$ is from about 130 to 180° C. and the second pressure $P_2$ is from about 50 to 100 bar. Similarly, the first hydrocarbon-containing gas stream 26 is characterized by a third temperature $T_3$ and a third pressure $P_3$. In a refinement, the third temperature $T_3$ is from about 100 to 180° C. and the third pressure $P_3$ is from about 50 to 100 bar. Advantageously, recycle gas stream 22 is obtained from 2-phase separator 28 as explained below in more detail. The recycle gas stream 22 flows through recycle conduit 29 which may have compressor-2 included therein.

FIG. 1B provides an example of various input compositions for the components of the system of FIG. 1A. FIG. 1C provides an example of various flow rates for the system of FIG. 1A. FIG. 1D provides an example of parameters for a natural gas feed for the system of FIG. 1A.

Sill referring to FIG. 1A, first hydrocarbon-containing gas stream 26 is preheated to form a second hydrocarbon-containing gas stream 34 having a fourth temperature $T_4$ that is greater than the third temperature. The first hydrocarbon-containing gas stream can be preheated by recovering energy generated from a partial oxidation reactor in order to preheat incoming hydrocarbon feed to the partial oxidation reactor (e.g., reactor 40). In a refinement, such preheating can be accomplished by the heat exchanger 30. In another refinement, the second hydrocarbon-containing gas stream 34 is also characterized by a fourth pressure $P_4$. In a refinement, the fourth temperature $T_4$ is from about 350 to 450° C. and the second pressure $P_4$ is from about 50 to 100 bar.

A first substream 36 of second hydrocarbon-containing gas stream 34 is introduced into GLT reactor 40 (a type of partial oxidation reactor) with an oxygen-containing gas stream 38 form a first product stream 44. FIG. 1E provides an example of parameters for GLT reactor 40. One or more liquid oxygenated hydrocarbons (e.g., methanol, ethanol, etc.) are separated from the first product stream 44. FIG. 1F provides an example of useful GLT reactor conditions. In a refinement, one or more liquid oxygenated hydrocarbons (e.g., methanol, ethanol, etc.) are separated from the first product stream 144. In another refinement, the first product stream includes an alcohol selected from the group consisting of methanol, ethanol, propanols, butanols, pentanols, and combinations thereof. The first product stream can also include $C_{5-15}$ branch alcohols chain and cyclic alcohols. In a refinement, first product stream 44 passes through heat exchanger 30 to provide the preheating of first hydrocarbon-containing gas stream 26. In a refinement, this separation is accomplished using 2-phase separator 28. A fuel gas stream 48 and the recycle gas stream 22 from the first product stream. A substream 50 of the first hydrocarbon-containing gas stream and a second substream 52 of the second hydrocarbon-containing gas stream 34 to form a third hydrocarbon-containing gas stream 56 having a fifth temperature $T_5$ that is between the third temperature $T_3$ and the fourth temperature $T_4$. The third hydrocarbon-containing gas stream 56 is also characterized by a fifth pressure. In a refinement, the fifth temperature is from about 175 to 275° C. and the fifth pressure from about 10 to 30 bar when third hydrocarbon-containing gas stream 56 is introduced into the syngas reactor 60.

In a variation, each of first hydrocarbon-containing gas stream 26, second hydrocarbon-containing gas stream 34, third hydrocarbon-containing gas stream 56, and substreams thereof each independently include $C_{1-10}$ alkanes. Examples of such alkanes include but are not limited to methane, ethane, propanes, butanes, pentanes, and combinations thereof.

Still referring to FIG. 1A, third hydrocarbon-containing gas stream 56 and oxygen-containing stream 58 to a syngas reactor 60 that converts the third hydrocarbon-containing gas stream to syngas and/or turquoise hydrogen. In a refinement, syngas reactor 60 is a partial oxidation of methane reforming reactor also referred to as a POX reactor that form syngas according to the following equation:

$$CH_4+\frac{1}{2}O_2\times CO+2H_2\ \Delta H_{298}=-8.5\ \text{kcal/mol}$$

It should be appreciated that this a catalytic process (Ni is a most active catalyst for this reaction). FIG. 1B provides examples of input concentrations and output concentrations to the POX syngas reactor. Advantageously, the syngas meets the downstream requirements. In a refinement, both of oxygen-containing streams 38 and 58 are derived from the same oxygen source 66 through liquid oxygen pump 68, thermal flow controller 70, and three-way valve or controller 72. Finally, syngas can be collected from the syngas reactor 60. In a refinement, syngas and/or turquoise hydrogen can be collected from the syngas reactor.

In another embodiment, a gaseous composition that is provided to a POX syngas reactor is provided. The gaseous composition includes methane in a mole fraction from 0.65 to 0.8, ethane in a mole fraction from 0.1 to 0.3, propane in a mole fraction from 0.01 to 0.1, carbon dioxide in a mole fraction from 0.001 to 0.05, carbon monoxide in a mole fraction from 0.001 to 0.05, nitrogen in a mole fraction from 0.02 to 0.13, and hydrogen in a mole fraction from 0.001 to 0.05.

With reference to FIG. 2A, a schematic of a system having a DMR reactor is provided. System 110 includes source 112 of a hydrocarbon feedstock. Hydrocarbon feed gas stream 114 is established by natural gas compressor 116, the thermal flow controller 118, and valve 120. Hydrocarbon feed gas stream 114 is characterized by a first temperature $T_1$ and a first pressure $P_1$. In a refinement, first temperature $T_1$ is from about 70 to 90° C., and the first pressure $P_1$ is from about 50 to 100 bar. Hydrocarbon feed gas stream 114 is combined with recycle $CO_2$-lean gas stream 122 at a three-way valve or splitter 124 (or other gas combining component) to form a first hydrocarbon-containing gas stream 126. Recycle $CO_2$-lean gas stream 122 is characterized by a second temperature $T_2$ and a second pressure $P_2$. In a refinement, the second temperature $T_2$ is from about 130 to 180° C. and the second pressure $P_2$ is from about 50 to 100 bar. Similarly, the first hydrocarbon-containing gas stream 126 is characterized by a third temperature $T_3$ and a third pressure $P_3$. In a refinement, the third temperature $T_3$ is from about 100 to 180° C. and the third pressure $P_3$ is from about 50 to 100 bar. Advantageously, recycle $CO_2$-lean gas stream 122 is obtained from 2-phase separator 128 as explained below in more detail.

Still referring to FIG. 2A, a first substream of first hydrocarbon-containing gas stream 126 is preheated to form a second hydrocarbon-containing gas stream 134 having a fourth temperature $T_4$ that is greater than the third temperature $T_3$. In a refinement, such preheating can be accomplished by heat exchanger 130. In another refinement, the second hydrocarbon-containing gas stream 134 is also characterized by a fourth pressure $P_4$. In a refinement, the fourth temperature $T_4$ is from about 350 to 450° C. and the fourth pressure $P_4$ is from about 50 to 100 bar.

Second hydrocarbon-containing gas stream 134 is combined with a second substream 135 of first hydrocarbon-containing gas stream 126 to form third hydrocarbon-containing gas stream 136. Since second substream 135 of first hydrocarbon-containing gas stream 126 has a lower temperature than second hydrocarbon-containing gas stream 314, second substream 135 can be used to low the temperature of second hydrocarbon-containing gas stream 34 when needed. Third hydrocarbon-containing gas stream 136 is introduced into GLT reactor 140 (a type of partial oxidation reactor) with an oxygen-containing gas stream 138 form a first product stream 144. FIG. 2B shows an example of input and output concentrations to the various components of system 100 including GLT reactor 140. FIG. 2B provides an example of a natural gas feed to GLT reactor 140.

In a refinement, one or more liquid oxygenated hydrocarbons (e.g., methanol, ethanol, etc.) are separated from the first product stream 144. In a refinement, the first product stream includes an alcohol selected from the group consisting of methanol, ethanol, propanols, butanols, pentanols and combinations thereof. Advantageously, these liquid oxygenated hydrocarbons are collected for commercial applications. In a refinement, first product stream 144 passes through heat exchanger 130 to provide the preheating of the first hydrocarbon-containing gas stream 126. In a refinement, this separation is accomplished using 2-phase separator 128. A fuel gas stream 148 and a $CO_2$-rich gas stream 150 are obtained from the first product stream. Typically, fuel gas stream 148 and the $CO_2$-rich gas stream 150 have the same chemical compositions. Three-way valve or flow splitter 152 are used to separate the fuel gas stream 148 and a $CO_2$-rich gas stream 150. Advantageously, fuel gas stream 148 can be collected for commercial applications. $CO_2$-rich gas stream 150 is directed to $CO_2$ stripper 160 to form recycle $CO_2$-lean gas stream 122 and $CO_2$ stream 162 which can be collected for commercial applications. Recycle $CO_2$-lean gas stream 122 includes hydrocarbons such as methane, ethane, etc. $CO_2$ stream 162 or a substream thereof and fuel gas stream 148 or a substream thereof are directed to syngas reactor 170 that is used to form syngas. In a refinement, syngas reactor 170, which is dry methane reforming (DMR) reactor that form syngas according to the following equation $$CH_4 + CO_2 \leftrightharpoons 2H_2 + 2CO \quad \Delta H^0_{296K} = +247 \text{ kj/mol}$$

It should be appreciated that this a catalytic process (Ni is a most active catalyst for this reaction). FIG. 2B provides examples of input concentrations and output concentrations to the DMR syngas reactor. Advantageously, the syngas meets the downstream requirements. Finally, syngas and/or turquoise hydrogen can be collected from the syngas reactor 170. In a refinement, syngas can be collected from the syngas reactor.

In another embodiment, the CO produced from the syngas reactor (e.g., a DRM reactor and/or a POX reactor) can be used in a blast furnace either directly transporting the gas through a pipeline or by filled compressed cylinders. The iron ores such as haematite contain iron (III) oxide, Fe 203, which can be reduced to metallic iron by an iron ore reduction process to produce pig iron for construction:

Iron (III) oxide+carbon monoxide→iron+carbon dioxide $Fe_2O_3(s)+3CO(s) \rightarrow 2Fe(l)+3CO_2(g)$ The hot stream of CO coming out of the syngas reactor (e.g., a DRM reactor and/or a POX reactor) can be feed in to the blast furnace and the temperature of the CO stream can be in the range of 200-800° C. Iron oxide will partially reduce to Fe (III, II and oxides) at around 700-1200° C. the oxides will be reduced to pure metallic iron, commonly known as pig iron.

In a refinement, heat integration of the blast furnace with the GTL reactor, DRM and POX reactor will bring additional saving on the energy utilization and reduce overall $CO_2$ emission of the plant.

This $CO_2$ produced in the process can be recycled back in the syngas reactor (e.g., the DRM reactor) for producing CO and hydrogen. Consuming a portion of the CO from the syngas stream of the syngas reactor (e.g., a DRM reactor and/or a POX reactor) will increase the $H_2/CO$ ratio to >2, which meets the downstream requirement of FT fuels and methanol production. The CO utilization of the DRM/POX reactor-produced syngas in a blast furnace may be used as a syngas ratio adjuster in the reforming process.

In another embodiment, a gaseous composition that is provided to a DRM syngas reactor is provided. The gaseous composition includes methane in a mole fraction from 0.35 to 0.5, ethane in a mole fraction from 0.05 to 0.2, propane in a mole fraction from 0.01 to 0.1, carbon dioxide in a mole fraction from 0.3 to 0.06, carbon monoxide in a mole fraction from 0.005 to 0.05, nitrogen in a mole fraction from 0.005 to 0.05, and hydrogen in a mole fraction from 0.01 to 0.05.

In a variation of system 10 of FIG. 1A and of system 110 of FIG. 2A, oxygen is produced locally at oxygen station 66. In a refinement, oxygen station 66 outputs gaseous nitrogen with or without liquid nitrogen in addition to the oxygen used in syngas reactor 60. The liquid nitrogen can be sold if desired. The gaseous nitrogen can be used to generate electricity via a flow-driven generator 80. Typically, the flow-driven generator includes a flow-driven turbine 82. Characteristically, the nitrogen is at a pressure greater than 1 bar in order to rotate the turbine 82. In a refinement, the generated electricity is zero emissions and can be used in the syngas reactor 60 to make it more energy-efficient.

In a variation, a blast furnace 90 can be used as a syngas ratio adjuster for the partial oxidation reactor (e.g., a DRM or POX reactor). In a refinement, a syngas ratio of $CO:H_2$ is adjusted from 1:1 to 1:2 using the blast furnace downstream of the syngas reactor.

FIG. 3 provides a schematic of an integrated system and method for converting biomass to renewable natural gas that can be used in system 10 of FIG. 1A and system 110 of FIG. 2A. The numbers in circles in FIG. 3 indicated the sequence of steps. Conversion system 200 includes a compressor 202 that biomass gases receive gases (e.g., methane) from a biomass source 204. In a variation, biomass source 204 can be replaced by a blast furnace (not a biomass source). Examples of sources include landfills, products of an ag digester, producer gas from a biomass gasifier/coal gasifier/mixture of coal and biomass gasifier, and products of a wastewater treatment plant. The gaseous product is purified to a purified gas in a series of purification stations to enhance the amount of methane that will provide to a gas-to-liquids plant. Knockout tank 206 is in fluid communication with compressor 202 receiving gas therefrom. $H_2S$ removal station 208 receives gas from knockout tank 204 and removes hydrogen sulfide. VOC station 210 acts on the output gas from $H_2S$ removal station 208 to remove volatile organic compounds. Scrubber 220 then acts on the output gas from VOC station 210 to remove carbon dioxide and potentially additional hydrogen sulfide. The output gas from scrubber 220 is then passed to an amine scrubber 222 that can remove amines and additional carbon dioxide. The output gas from scrubber 220 is then passed through molecular sieve system 230 to remove additional impurities. Nitrogen removal system 232 receives the output gas from molecular sieve system 230 and removes at least a portion of nitrogen gas. In a refinement, either a PSA or membrane separation process can be used to remove nitrogen. The outputs of any of VOC station 210, Scrubber 220, amine scrubber 222, molecular sieve system 230, and/or nitrogen removal system 232 provide natural gas (e.g., a methane-containing gas) that can be used as at least a component of the hydrocarbon feedstocks set forth above.

In a variation, the output gas from nitrogen removal system 232 is received by reciprocating compressor 234, which after compression is passed to GLT plant 236 where it is reacted with oxygen from an oxygen source 238 as set forth above. In a refinement, GTL plant can output a product blend 240. GTL plant 236 can be the GLT system set forth in U.S. Pat. No. 9,255,051; the entire disclosure of which is hereby incorporated by reference.

The product blend 240 advantageously includes methanol and ethanol. In a refinement, the product blend can also include hydrogen ($H_2$), acetone, dimethyl ether, isopropanol, acetic acid, formic acid, formaldehyde, dimethoxymethane, 1,1 dimethoxyethane, methyl formate, methyl acetate, and water. In another refinement, product blend includes 0 to 15 mole percent acetone, 30 to 99 mole percent methanol, 0 to 20 mole percent ethanol, 0.0 to 10 mole percent isopropanol, 0 to 1 mole percent acetic acid, 0 to 1 mole percent formic acid, 0 to 15 mole percent formaldehyde, and 1 to 30 mole percent water.

Advantageously, the integrated system of FIG. 3 has a carbon intensity that is less than +100 at its highest range depending on feedstock, and more typically +20 and typically, less than +15, with some feedstocks showing CI score less than −250 when using Ag digester dairy and pig farm gas.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention

What is claimed is:

1. A method for preparing oxygenated hydrocarbons, comprising:

a) combining a hydrocarbon feed gas stream and a recycle gas stream to form a first hydrocarbon-containing gas stream, the hydrocarbon feed gas stream having a first temperature, the recycle gas stream having a second temperature, and the first hydrocarbon-containing gas stream having a third temperature;

b) preheating the first hydrocarbon-containing gas stream to form a second hydrocarbon-containing gas stream having a fourth temperature that is greater than the third temperature;

c) reacting the second hydrocarbon-containing gas stream with a first oxygen-containing gas stream in a partial oxidation reactor to form a first product stream;

d) separating and condensing one or more liquid oxygenated hydrocarbons from the first product stream;

e) separating a fuel gas stream and the recycle gas stream from the first product stream;

f) combining a portion of the first hydrocarbon-containing gas stream and a portion of the second hydrocarbon-containing gas stream to form a third hydrocarbon-containing gas stream having a fifth temperature that is between the third temperature and the fourth temperature;

g) directing the third hydrocarbon-containing gas stream and second oxygen-containing gas stream to a syngas reactor that converts the third hydrocarbon-containing gas stream to syngas and/or turquoise hydrogen; and h) collecting syngas and/or turquoise hydrogen from the syngas reactor.

2. The method of claim 1 wherein the first hydrocarbon-containing gas stream is preheated by recovering energy generated from the partial oxidation reactor in order to preheat incoming hydrocarbon feed to the partial oxidation reactor.

3. The method of claim 1 wherein the syngas reactor is a partial oxidation of methane (POM) reactor.

4. The method of claim 1 wherein the first temperature is from about 70 to 90° C., the hydrocarbon feed gas stream is at a pressure from about 50 to 100 bar, the second temperature is from about 130 to 180° C., the recycle gas stream is at a pressure from about 50 to 100 bar, the third temperature is from about 100 to 180° C., the first hydrocarbon-containing gas stream is at a pressure from about 50 to 100 bar, the fourth temperature is from about 350 to 450° C., and the second hydrocarbon-containing gas stream is at a pressure from about 50 to 100 bar, the fifth temperature is from about 175 to 275° C., and the third hydrocarbon-containing gas stream has a pressure from about 10 to 30 bar when directed to the syngas reactor.

5. The method of claim 4 wherein pressure of the portion of the first hydrocarbon-containing gas stream and pressure of the portion of the second hydrocarbon-containing gas stream are reduced prior to forming the third hydrocarbon-containing gas stream.

6. The method of claim 1 wherein the first hydrocarbon-containing gas stream includes $C_{1-10}$ alkanes.

7. The method of claim 1 further comprising collecting the first product stream.

8. The method of claim 7 wherein the first product stream includes an alcohol selected from the group consisting of methanol, ethanol, propanols, butanols, pentanols and combinations thereof.

9. The method of claim 1 wherein the hydrocarbon feed gas stream is received from an integrated system comprising:

a compressor that receives biomass gases from a biomass source;

a series of purification stations that produces a purified gas from the biomass gases, the purified gas having an enhanced amount of methane; and a gas-to-liquids plant that converts the purified gas to a product blend that includes methanol.

10. The method of claim 9, wherein the biomass source include landfills, an ag digester, producer gas from a biomass gasifier/coal gasifier/mixture of coal and biomass gasifier and a wastewater treatment plant.

11. The method of claim 9, wherein the series of purification stations includes a knockout tank that receives gas from the compressor, a $H_2S$ removal station that receives gas from knockout tank and removes hydrogen sulfide, a VOC station that acts on an output gas from $H_2S$ removal station 16 to remove volatile organic compounds, a scrubber that acts on an output gas from VOC station to remove carbon dioxide and potentially additional hydrogen sulfide, an amine scrubber that receives an output gas from the scrubber that can remove amines and additional carbon dioxide, a molecular sieve system that receives output gas from scrubber to remove additional impurities, a nitrogen removal system that receives output gas from the molecular sieve system and removes at least a portion of nitrogen gas therein, a reciprocating compressor that receives output gas from the nitrogen removal system and then, after compression, passes the gas to the gas-to-liquids plant.

12. The method of claim 9, wherein the product blend includes methanol, dimethyl ether, and hydrogen.

13. The method of claim 1, wherein the first oxygen-containing gas stream and/or the second oxygen-containing gas stream is produced at an oxygen station that separates gaseous nitrogen with or without liquid nitrogen in addition to oxygen used in syngas reactor.

14. The method of claim 13, wherein gaseous nitrogen can be used to generate electricity via a flow-driven generator.

15. The method of claim 11 further comprising using CO from a gas stream produced by the syngas reactor in an iron ore reduction process to process hematite iron ore to produce pig iron for construction.

16. The method of claim 15 wherein $CO_2$ produced in the iron ore reduction process can be recycled back to a DRM reactor to produce syngas thus reducing $CO_2$ emission.

17. A method for preparing oxygenated hydrocarbons, comprising:

a) combining a hydrocarbon feed gas stream and a $CO_2$ lean recycle gas stream to form a first hydrocarbon-containing gas stream, the hydrocarbon feed gas stream having a first temperature, the $CO_2$ lean recycle gas stream having a second temperature, and the first hydrocarbon-containing gas stream having a third temperature;

b) preheating the first hydrocarbon-containing gas stream to form a second hydrocarbon-containing gas stream having a fourth temperature that is greater than the third temperature;

c) reacting the second hydrocarbon-containing gas stream with a first oxygen-containing gas stream in a partial oxidation reactor to form a first product stream;

d) separating and condensing one or more liquid oxygenated hydrocarbons from the first product stream;

e) separating a fuel gas stream and a $CO_2$ rich recycle gas stream from the first product stream;

f) removing $CO_2$ from the $CO_2$ rich recycle gas stream to form the $CO_2$ lean recycle gas stream;

g) combining a portion of the $CO_2$ lean recycle gas stream and a portion of the fuel gas stream to form a third hydrocarbon-containing gas stream;

h) directing the third hydrocarbon-containing gas stream and a second oxygen-containing gas stream to a syngas reactor to form syngas and/or turquoise hydrogen; and i) collecting syngas and/or turquoise hydrogen from the syngas reactor.

18. The method of claim 17 wherein the first hydrocarbon-containing gas stream is preheated by recovering energy generated from the partial oxidation reactor in order to preheat incoming hydrocarbon feed to the partial oxidation reactor.

19. The method of claim 17 wherein the syngas reactor is a DMR reactor that form syngas according to the following equation:

$$CH_4+CO_2 \rightleftharpoons 2H_2+2CO.$$

20. The method of claim 17 wherein the first temperature is from about 70 to 90° C., the hydrocarbon feed gas stream is at a pressure from about 50 to 100 bar, the second temperature is from about 130 to 180° C., the $CO_2$ lean recycle gas stream is at a pressure from about 50 to 100 bar, the third temperature is from about 100 to 180° C., the first hydrocarbon-containing gas stream is at a pressure from about 50 to 100 bar, the fourth temperature is from about 350 to 450° C., the second hydrocarbon-containing gas stream is at a pressure from about 50 to 100 bar.

21. The method of claim 20 wherein the first hydrocarbon-containing gas stream includes $C_{1-10}$ alkanes.

22. The method of claim 17 further comprising collecting the first product stream.

23. The method of claim 22 wherein the first product stream includes an alcohol selected from the group consisting of methanol, ethanol, propanols, butanols, pentanols and combinations thereof.

24. The method of claim 17, wherein the hydrocarbon feed gas stream is received from an integrated system comprising:

a compressor that receives biomass gases from a biomass source;

a series of purification stations that produces a purified gas from the biomass gases, the purified gas having an enhanced amount of methane; and a gas-to-liquids plant that converts the purified gas to a product blend that includes methanol.

25. The method of claim 24, wherein the series of purification stations includes a knockout tank that receives gas from the compressor, a $H_2S$ removal station that receives gas from knockout tank and removes hydrogen sulfide, a VOC station that acts on an output gas from $H_2S$ removal station to remove volatile organic compounds, a scrubber that acts on an output gas from VOC station to remove carbon dioxide and potentially additional hydrogen sulfide, an amine scrubber that receives an output gas from the scrubber that can remove amines and additional carbon dioxide, a molecular sieve system that receives output gas from scrubber to remove additional impurities, a nitrogen removal system that receives output gas from the molecular sieve system and removes at least a portion of nitrogen gas therein, a reciprocating compressor that receives output gas from the nitrogen removal system and then, after compression, passes the gas to the gas-to-liquids plant.

* * * * *